United States Patent [19]

Adams et al.

[11] Patent Number: 5,955,367
[45] Date of Patent: *Sep. 21, 1999

[54] PRODUCTION OF BACILLUS THURINGIENSIS INTEGRANTS

[75] Inventors: Lee Fremont Adams; Michael David Thomas; Alan P. Sloma; William R. Widner, all of Davis, Calif.; Steen Troels Jørgensen, Allerød, Denmark; Per Linå Jørgensen, Copenhagen K, Denmark; Børge Krag Diderichsen, Birkerød, Denmark

[73] Assignee: Abbott Laboratories, Abbott Park, Ill.

[ * ] Notice: This patent is subject to a terminal disclaimer.

[21] Appl. No.: 09/060,288

[22] Filed: Apr. 14, 1998

Related U.S. Application Data

[63] Continuation of application No. 08/378,236, Jan. 25, 1995, abandoned, which is a continuation-in-part of application No. 08/274,608, Jul. 13, 1994, which is a continuation-in-part of application No. 08/092,338, Jul. 15, 1993, abandoned, and a continuation-in-part of application No. 07/853,701, May 26, 1992, abandoned.

[30] Foreign Application Priority Data

Dec. 18, 1989 [DK] Denmark ................................. 6396/89

[51] Int. Cl.⁶ .............................. C12N 1/21; C12N 15/32; C12N 15/74; C12N 15/90

[52] U.S. Cl. ........................ 435/485; 435/69.1; 435/71.2; 435/252.31; 435/320.1

[58] Field of Search ......................... 435/172.3, 252.31, 435/69.1, 320.1, 71.2, 485

[56] References Cited

U.S. PATENT DOCUMENTS 5,695,976  12/1997  Jørgensen et al. .................... 435/172.3

FOREIGN PATENT DOCUMENTS 0 127 328  of 0000  European Pat. Off. .

OTHER PUBLICATIONS

Hofemeister et al., Mol. Gen. Genet. 189:58–68.
Arantes et al., Gene 108:115–119 (1991).
Baum et al., Applied and Environmental Microbiology 56(11):3420–3428 (1990).

*Primary Examiner*—Johnny F. Railey, II
*Attorney, Agent, or Firm*—Michael J. Ward; Dugal S. Sickert

[57] ABSTRACT

The invention relates to a method for producing an integrant (s) of *Bacillus thuringiensis*. The invention further relates to such integrants, compositions comprising such integrants, as well as methods for controlling a pest(s) using these compositions.

13 Claims, 5 Drawing Sheets

PRODUCTION OF BACILLUS THURINGIENSIS INTEGRANTS

This is a continuation of U.S. patent application Ser. No. 08/378,236, filed Jan. 25, 1995 now abandoned, which is a continuation-in-part of co-pending application Ser. No. 08/274,608, filed Jul. 13, 1994, which is a continuation-in-part of application Ser. No. 08/092,338, filed Jul. 15, 1993, now abandoned. This application is also a continuation-in-part of application Ser. No. 07/853,701, filed May 26, 1992, now abandoned, which claims benifit of PCT/DK90/00332, filed Dec. 18, 1990.

FIELD OF THE INVENTION

The invention relates to methods for obtaining an integrant(s) of *Bacillus thuringiensis*. The invention further relates to such integrant(s), or spores thereof, compositions comprising such integrant(s), as well as methods for controlling a pest(s) using these compositions.

BACKGROUND OF THE INVENTION

Pests may be controlled using either chemical pesticides or biopesticides. However, because of their broad spectrum of activity, chemical pesticides may destroy non-target organisms such as beneficial insects and parasites and predators of destructive pests. Additionally, chemical pesticides are frequently toxic to animals and humans. Furthermore, targeted pests frequently develop resistance when repeatedly exposed to such substances.

Biopesticides make use of naturally occurring pathogens to control insect, fungal and weed infestations of crops. An example of a biopesticide is a bacterium which produces a substance toxic to the infesting pest A biopesticide is generally less harmful to non-target organisms and the environment as a whole than chemical pesticides.

The most widely used biopesticide is *Bacillus thuringiensis*. *Bacillus thuringiensis* is a motile, rod-shaped, gram-positive bacterium that is widely distributed in nature, especially in soil and pest-rich environments. During sporulation, *Bacillus thuringiensis* produces a parasporal crystal inclusion(s) which is toxic upon ingestion to susceptible larvaea. The inclusion(s) may vary in shape, number, and composition. They are comprised of one or more proteins called delta-endotoxins, which may range in size from 27–140 kDa The delta-endotoxins are generally converted by proteases in the larval gut into smaller (truncated) toxic polypeptides, causing midgut destruction, and ultimately, death of the pest (Höfte and Whiteley, 1989, *Microbiol. Rev.* 53:242–255).

The delta-endotoxins are encoded by cry (crystal protein) genes. The cry genes have been divided into six classes and several subclasses based on relative amino acid homology and pesticidal specificity. The six major classes are Lepidoptera-specific (cryI), Lepidoptera- and Diptera-specific (cryII), Coleoptera-specific (cryIII), Diptera-specific (cryIV) (Höfte and Whiteley, 1989, *Microbiol. Rev.* 53:242–255), Coleoptera- and Lepidgptera-specific (referred to as cryV genes by Tailor et al., 1992, *Mol. Microbiol.* 6:1211–1217); and Nematode-specific (referred to as cryV and cryVI genes by Feitelson et al., 1992, *Bio/Technology* 10:271–275). Several *Bacillus thuringiensis* crystal delta-endotoxins are also reportedly pesticidal to Acari, Hymenoptera, Phthiraptera, Platyheiminthes, Homoptera, Blattodea, and Protozoa.

Delta-endotoxins have been produced by recombinant DNA methods. The delta-endotoxins produced by recombinant DNA methods may or may not be in crystal form. Various cry genes have been cloned, sequenced, and expressed in various hosts, e.g., *E. coli* (Schnepf et al., 1987, *J. Bacteriol.* 169:4110–4118) and *Bacillus subtilis* (Shivakamar et al., 1986, *J. Bacteriol.* 166:194–204).

Amplification of cry genes has been achieved in *Bacillus subtilis*. The delta-endotoxin gene of *Bacillus thuringiensis* subsp. *kurstaki* HD73 has been cloned into *Bacillus subtilis* using an integrative plasmid and amplified (Calogero et al., 1989, *Appl. Environ. Microbiol.* 55:446–453). However, no increase in crystal size was observed as compared to *Bacillus thuringiensis* subsp. *kurstaki* HD73. Furthermore, no difference in pesticidal activity was reported.

The level of expression of delta-endotoxin genes appears to be dependent on the host cell used (Skivakamar et al., 1989, *Gene* 79:21–31). For example, Skivakumar et al. found significant differences in the expression of the cryIA and cryIIA delta-endotoxin genes of *Bacillus thuringiensis* subsp. *kurstaki* in *Bacillus subtilis* and *Bacillus megaterium*. The cryIA gene was expressed when present on a multicopy vector in *Bacillus megaterium*, but not in *Bacillus subtilis*. The cryIIA gene was expressed in both hosts, but at a higher level in *Bacillus megaterium*. Sections of *Bacillus megaterium* cells expressing these delta-endotoxin genes were examined by electron microscopy; the presence of large bipyramidal crystals in these cells was detected. However, there is no indication that these crystals are any larger than crystals found in *Bacillus thuringiensis* subsp. *kurstaki* which normally contain these genes. Results from bioassays of the *Bacillus megaterium* cells expressing these delta-endotoxin genes indicate that there was no increase in pesticidal activity as compared to *Bacillus thuringiensis* subsp. *kurstaki*. Indeed, five times the concentration of *Bacillus megaterium* than *Bacillus thuringiensis* subsp. *kurstaki* was required to obtain the same insect killing effect.

In the prior art methods, a host cell is transformed with a recombinant DNA vector carrying a DNA sequence encoding a delta-endotoxin and DNA replication sequences. The expression of the delta-endotoxin is dependent on the replication of the recombinant DNA vector in the host. When, for the purpose of producing a desired polypeptide by recombinant DNA procedures, bacterial cells are transformed with a recombinant plasmid vector which carries inserted genetic information coding for the delta-endotoxin, it has often been observed that such plasmids become unstable even though they may, in themselves, be stably inherited in the cell. This instability may either take the form of unstable maintenance of the plasmid in the cells so that the plasmid will eventually be lost from a cell population, or so that the DNA coding for the protein in question may be deleted from the plasmid. A traditional way of solving the former problem has been to grow the transformed cells under selection pressure, that is, typically in the presence of an antibiotic to which the cells in question have been made resistant due to the presence of a gene coding for a product mediating resistance to that antibiotic on the plasmid transformed to the cells. This approach, however, is neither economically feasible in large-scale production due to the high cost of the antibiotics in question, nor is it desirable for environmental reasons. The use of antibiotics in culture media also makes it more difficult to obtain product approval from health authorities and the like.

It has previously been suggested that plasmids could be stabilized by inserting into them a DNA sequence encoding a partitioning function which ensures the even distribution of plasmids to progeny cells on cell division. An alternative method of achieving the stable inheritance of cloned DNA sequences is to provide for the integration of such DNA sequences in the genome of the host bacterium. Integration of DNA sequences present on plasmid vectors may take place by the so-called "crossing-over" procedure, e.g. as described by A. Campbell, *Advances Genet.* 11, 1962, pp. 101–145. According to this procedure, the plasmid. vector is provided with a DNA sequence which is homologous to a region on the bacterial genome, or alternatively with two homologous sequences placed on either side of the heterologous DNA sequence to be integrated. In a subsequent recombination event, the homologous sequence and adjacent sequences on the vector are integrated into the host genome at the region of homology.

In some cases, however, it has been found that the integrated DNA sequences are deleted from the cells in the absence of selection pressure, for instance by a similar type of homologous recombination event as that responsible for the integration of the DNA. In particular, it has previously been observed that recombination between homologous DNA sequences is stimulated in the proximity of replicative DNA present on or near the DNA integrated in the host cell genome, cf. Ph. Noirot et al., *J. Mol. Biol.* 196, 1987, pp. 39–48; and M. Young and S. D. Ehrlich, *J. Bacteriol.* 171(5), May 1989, pp. 2653–2656.

An object of the present invention is therefore to provide stable integration of DNA sequences into genomic DNA, e.g. the chromosome, of bacterial, particularly *Bacillus thuringiensis* host cells. It is also an object of the invention to create integrants of *Bacillus thuringiensis* strains which produce sufficient quantities of delta-endotxins. Such integrants may be usefull in broadening the host range of *Bacillus thuringiensis* and obtaining more effective formulations of *Bacillus thuringiensis*.

SUMMARY OF THE INVENTION

The present invention relates to methods for obtaining an integrant of *Bacillus thuringiensis* which produces at least one heterologous crystal delta-endotoxn. The integrant is obtained by
  (a) introducing into a cell of a host *Bacillus thuringiensis* strain (i) a first DNA vector comprising a first origin of replication and at least one functional gene encoding at least one factor required for plasmid replication from said first origin of replication, and with (ii) a second DNA vector comprising a second origin of replication but lacidng a functional gene encoding a factor required for plasmid replication from the second origin of replication, as well as a DNA sequence encoding a *Bacillus thuringiensis* delta-endotoxin, a DNA sequence that is homologous with a region of the genome of said host strain, and a selectable marker and
  (b) culturing the cell of step (a) under selective conditions leading to the loss of the first DNA vector and integration of said second DNA vector into the genome of said host cell by homologous recombination.
In a specific embodiment, the host *Bacillus thuringiensis* strain is a cry⁻strain The invention further relates to said integrant. The DNA sequence encoding the *Bacillus thuringiensis* delta-endotoxin may be a heterologous DNA sequence. In one embodiment, the integrant may in addition to comprising a heterologous crystal delta-endotoxin may also comprise a homologous crystal delta-endotoxin, a delta-endotoxin which is endogenously produced by the host *Bacillus thuringiensis* strain. In another embodiment, the integrant may produce more than one heterologous *Bacillus thuringiensis* delta-endotoxin. In another embodiment, a larger quantity of a crystal delta-endotoxin with greater pesticidal activity and optionally a larger crystal size as a result of gene amplification or hyperexpression is produced as compared to the corresponding parental strain.

The invention also relates to a pesticidal composition comprising such an integrant and a pesticidally acceptable carrier as well as methods for controlling a pest(s) using such a composition.

DEFINITIONS

"Integrant" as defined herein is a *Bacillus thuringiensis* strain containing an additional DNA segment (generally, a cry gene, antibiotic resistance gene, and plasmid-associated DNA) inserted into the genome of said strain by homologous recombination.

A "heterologous DNA sequence" as defined herein is a DNA sequence which does not naturally occur in the host *Bacillus thuringiensis* cell.

A "genome" as defined herein is all DNA, both chromosomal and plasmid, within a *Bacillus thuringiensis* cell.

"Parental strain" as defined herein is the strain that is the source of the heterologus DNA sequence encoding the *Bacillus thuringiesis* delta-endotoxin.

"Greater pesticidal activity" as defined herein means at least 1.25 times more activity against a pest, through killing or stunting of the growth of the pest, than the corresponding parental strain. In a preferred embodiment, the pesticidal activity of the integrant is between about 1.5 to about 10 times greater than the pesticidal activity of the corresponding parental *Bacillus thuringiensis* strain.

"Larger quantity" as defined herein means that the integrant produces at least 1.25 times the amount of a crystal delta-endotoxin as the parental strain.

"Larger crystal size" as defined herein means that the largest face of the crystal of the integrant has at least 1.2 times the surface area or volume of the crystal of the parental strain.

DETAILED DESCRIPTION OF THE INVENTION

Methods for Obtaining Integrants

Figure 1:
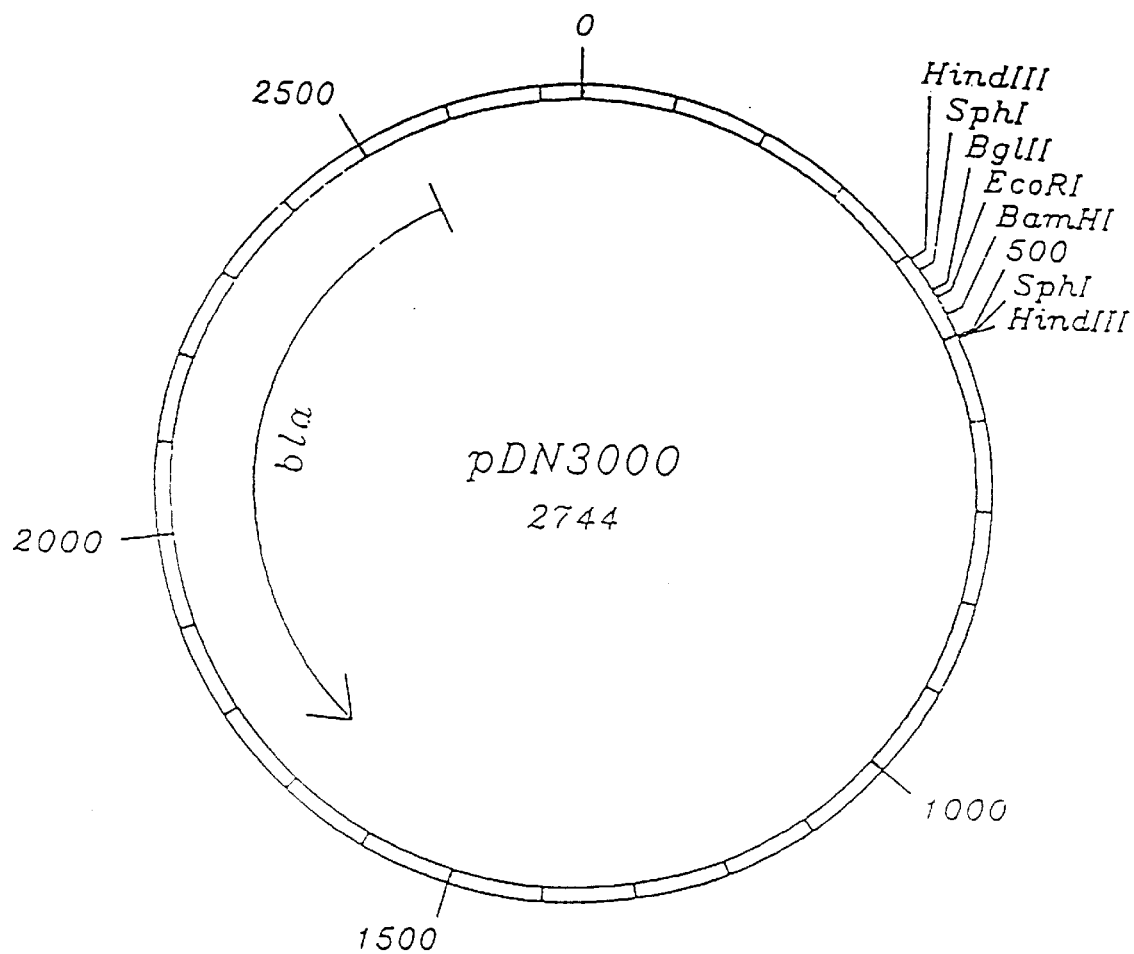
FIG. 1 shows a map of plasmid pDN3000.

The integrant of the present invention can be obtained by a "two-plasmid" integration system. This system relies on a first or helper plasmid, which comprises an origin of replication and at least one functional gene encoding at least one factor requried for plasmid replication, e.g., a temperature sensitive replication protein which functions in trans, and a second vector or an integrative plasmid, which cannot replicate in the absence of the helper plasmid. The integrative plasmid of the present invention comprises (i) a cry gene, (ii) a region of homology with the host genome (for example, the 16S rRNA gene or the phospholipase C gene or cry gene itself), and (iii) a selectable marker. The first plasmid may also comprise a DNA sequence which encodes a selectable marker, e.g., an antibiotic resistance marker which differs from that encoded by the helper plasmid. The helper plasmid may be added before or simultaneously with the integrative plasmid.

In a specific embodiment, the helper plasmid is introduced, by electroporation, into the desired host, including but not limited to *Bacillus thuringiensis* subsp. *kurstaki*, *Bacillus thuringiensis* subsp. *aizawai*, *Bacillus thuringiensis* subsp. *galleriae*, *Bacillus thuringiensis* subsp. *entomocidus*, *Bacillus thuringiensis* subsp. *tenebrionis*, *Bacillus thuringiensis* subsp. *thuringiensis*, *Bacillus thuringiensis* subsp. *alesti*, *Bacillus thubngiensis* subsp. *canadiensis*, *Bacillus thuringiensis* subsp. *dartstadiensis*, *Bacillus thuringiensis* subsp. *dendrolimus*, *Bacillus thuringiensis* subsp. *finitimus*, *Bacillus thuringiensis* subsp. *kenyae*, *Bacillus thuringiensis* subsp. *morrisoni*, *Bacillus thuringiensis* subsp. *subtoxicus*, *Bacillus thuringiensis* subsp. *toumanoffi*, *Bacillus thuringiensis* subsp. *toumanoffi*, *Bacillus thuringiensis* subsp. *pondicheriensis*, *Bacillus thuringiensis* subsp. *shandogiensis*, *Bacillus thuringiensis* subsp. *sotto*, *Bacillus thuringiensis* subsp. *nigeriae*, *Bacillus thuringiensis* subsp. *yunnanensis*, *Bacillus thuringiensis* subsp. *dakota*, *Bacillus thuringiensis* subsp. *indiana*, *Bacillus thuringiensis* subsp. *tohokuensis*, *Bacillus thuringiensis* subsp. *kumamotoensis*, *Bacillus thuringiensis* subsp. *tochigiensis*, *Bacillus thuringiensis* subsp. *thompsoni*, *Bacillus thuringiensis* subsp. *wuhanensis*, *Bacillus thuringiensis* subsp. *kyushuensis*, *Bacillus thuringiensis* subsp. *ostriniae*, *Bacillus thuringiensis* subsp. *tolworthi*, *Bacillus thuringiensis* subsp. *pakistani*, *Bacillus thuringiensis* subsp. *japonensis*, *Bacillus thuringiensis* subsp. *colmeri*, *Bacillus thuringiensis* subsp. *pondicheriensis*, *Bacillus thuringiensis* subsp. *shandongiensis*, *Bacillus thuringiensis* subsp. *neoleonensis*, *Bacillus thuringiensis* subsp. *coreanensis*, *Bacillus thuringiensis* subsp. *silo*, *Bacillus thuringiensis* subsp. *mexcanensis*, and *Bacillus thuringiensis* subsp. *israelensis* and maintained by the addition of a selection agent, for example, an antibiotic such as erythromycin, at a temperature which permits proper functioning of the temperature sensitive Rep protein (e.g., 30° C.). Then, the integrative plasmid lacking a functional replication protein (e.g., Rep protein) is introduced into the same host strain, and maintained by selection with a selecting agent, e.g., chloramphenicol. Selection with chloramphenicol alone is sufficient to maintain both plasmids because the integrative plasmid cannot exist without the helper plasmid. Growth at a higher temperature, e.g., 37° C., does not permit replication of the helper plasmid. In the absence of the helper plasmnid, the integrative plasmid, encoding chloramphenicol resistance, also cannot replicate. Therefore, the only way that the host cell can maintain resistance to chloramphenicol is by integration of the integrative plasmid by a Campbell recombination event at the region of homology that it shares with the *Bacillus thuringiensis* genome. Consequently, the DNA is integrated into the genome of the host strain. In a specific embodiment the host strain is a cry⁻ strain. In a most specific embodiment, the host strain is a *Bacillus thuringiensis* subsp. *kurstaki* strain.

The DNA sequence encoding a delta-endotoxin may be selected from the group including, but not limited to, a cryI, cryII, cryIII, cryIV, cryV, or cryVI gene. In one embodiment, the DNA sequence encoding the delta-endotoxin comprises the cryIC gene. The cryIC gene encodes a delta-endotoxin specific for lepidopteran pests. The DNA sequence comprising the cryIC gene may be obtained from a strain of *Bacillus thuringiensis* subsp. *aizawai*. In a most specific embodiment, the cryIC DNA sequence is obtained from *Bacillus thuringiensis* subsp. *aizawai* strain EMCC0087.

The plasmids may be introduced into the host *Bacillus thuringiensis* strain by procedures known in the art, e.g., electroporation, protoplasting of cells, transduction, chemical transformation, and regeneration (Macaluso and Mettus, 1991, *J. Bacteblol.* 173:1353–1356; Crawford et al., 1987, *J. Bacteriol.* 169:5423–5428; and Battisti et al, 1985, *J. Bacteriol.* 162:543–550). Simultaneous growth at a suitable temperature, e.g., 37° C. or higher, and antibiotic pressure selects for integration of the plasmid into the genome of the host cell by recombination with a homologous region of the genome of the host cell. The cell, which in its genome carries the integrated DNA construct, is grown in a medium with increasing amounts of an agent that selects for the selectable marker, e.g., media containing an antibiotic, thereby amplifying the selectable marker and, necessarily, the cry gene as well (Albertini and Galizzi, 1985, *J. Bacteriol.* 162:1203–1211).

In a preferred embodiment, the DNA encoding the delta-endotoxin is amplified in the integrant In a specific embodiment, such amplification occurs by transferring the integrant to medium comprising greater amounts of an agent that selects for the selectable marker. This step may be repeated several times with increasing amounts of the agent selecting for the selectable marker.

The integrant of the present invention may be cultured using media and fermentation techniques known in the art (see, for example, Rogoff et al., 1969, *J. Invertebrate Path.* 14:122–129; Dulmage et al., 1971, *J. Invertebrate Path.* 18:353–358; Duage et al., in *Microbial Control of Pests and Plant Diseases*, H. D. Burges (ed.), Academic Press, New York, 1980). Upon completion of the fermentation cycle, the *Bacillus thuringiensis* crystal delta-endotoxin(s) and spores can be harvested from the fermentation broth by means well known in the art, e.g., centrifugation.

Purification of the spores or delta-endotoxins produced by the integrant strain of the present invention can be carried out by various procedures known in the art including, but not limited to, ultrafiltration, differential extraction, density gradient centrifugation, chromatography, or other techniques for protein and/or particle purification.

The activity of the crystal delta-endotoxin or spores of the integrant strain of the present invention against various pests may be bioassayed using procedures known in the art, such as artificial diet incorporation, artificial diet overlay, leaf painting, leaf dip, foliar spray, and aquatic assay.

Compositions

The integrant *Bacillus thuringiensis* strains, crystal delta-endotoxins and/or spores of the invention, can be formulated into a pesticidal composition(s), that is, for example, a suspension, a dispersion, an aqueous emulsion, a dusting powder, a dispersible powder, an emulsifiable concentrate, an aerosol or micro or macroencapulated granules or any other formulation that gives controlled release of *Bacillus thuringiensis*. Such compositions may be obtained by the addition of a surface active agent, e.g., a dispersing agent, emulsifying agent or wetting agent, or an inert carrier or other component to facilitate handling and application for particular target pests.

Suitable surface-active agents include anionic compounds such as a carboxylate, for example, a metal carboxylate of a long chain fatty acid; a N-acylsarcosinate; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl-naphthalene sulphonate; salts or sulphonated naphthalene-formaldehyde condensates or salts of polyacrylic acid; salts of sulphonated phenol-formaldehyde condensates; or more complex sulphonates such as the amnide sulphonates, e.g., the sulphonated condensation product of oleic acid and N-methyl taurine or the dialkyl sulphosuccinates, e.g., the sodium sulphonate or dioctyl succinate. Non-ionic agents include condensation products of fatty acid esters, fatty alcohols, fatty acid amides or fatty-alkyl- or alkenyl-substituted phenols with ethylene oxide and/or propylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine as an acetate, naphthenate or oleate; an oxygen-containing amine such as an amine oxide of polyoxyethylene alkylamnine; an amide-linked amine prepared by the condensation of a carboxylic acid with a di- or polyamine; or a quaternary ammonium salt.

Examples of inert materials include inorganic minerals such as phyllosilicates, carbonates, sulfates, phosphates; organic materials such as sugar, starches, or cyclodextins; or botanical materials such as powdered corncobs, rice hulls, walnut shells, cornmeal, pelleted grains, and cellulosic fibers.

The compositions of the present invention can be in a suitable form for direct application or as a concentrate or primary composition which requires dilution with a suitable quantity of water or other diluent before application. The pesticidal concentration will vary depending upon the nature of the particular formulation, specifically, whether it is a concentrate or to be used directly. The composition contains 0.1% to 99%, preferably 0.1% to 95% of the integrant, mutant or variant of the present invention, 1 to 98% of a solid or liquid inert carrier, and 0 to 50%, preferably 0.1% to 50% of a surfactant. These compositions will be administered at about 0.01 lb–5.0 lb per acre when in dry form and at about 0.01 pt–10 pts per acre when in liquid form.

In a further embodiment, the integrants of the present invention can be treated prior to formulation to prolong the pesticidal activity when the cells are applied to the environment of a target pest. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropranol and ethanol; histological fixatives, such as Bouin's fixative and Helly's fixative (see, for example, Humason, *Animal Tissue Techniques*, W. H. Freeman and Co., 1967); preservatives; UV sunscreens; spray adjuvants (humectants); antifoams; and stickers.

The compositions of the invention can be applied directly to the plant by, for example, spraying or dusting at the time when the pest has begun to appear on the plant or before the appearance of pests as a protective measure. Plants to be protected within the scope of the present invention include, but are not limited to, cereals (wheat, barley, rye, oats, rice, sorghum and related crops), beet (sugar beet and fodder beet), drupes, pomes and soft fruit (apples, pears, plums, peaches, almonds, cherries, strawberries, raspberries, and blackberries, tomatoes), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages and other *brassicae*, carrots, onions, potatoes, paprika), *lauraceae* (avocados, cinnamon, camphor), deciduous trees and conifers (linden-trees, yew-trees, oak-trees, alders, poplars, birch-trees, firs, larches, pines), or plants such as maize, tobacco, nuts, coffee, sugar cane, tea, vines hops, bananas and natural rubber plants, as well as ornamentals. The preferred mode of application is by foliar spraying. It is generally important to obtain good control of pests in the early stages of plant growth as this is the time when the plant can be most severely damaged. The spray or dust can conveniently contain another insecticide or pesticide, e.g., fungicide, grass herbicide or fertilizer, if this is thought necessary. In a preferred embodiment, the composition of the invention is applied directly to the plant.

The compositions of the present invention may be effective against pests of the order Lepidoptera, e.g., *Achroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis,* Archips sp., Argyrotaenia sp., *Athetis mindara, Bombyx mori, Biicculatrix thurberiella, Cadra cautella,* Choristoneura sp., *Cochylis hospes, Colias eluytheme, Corcyra cephalonica, Cydia latiferreanus, Cydia pomonella, Datana integerrima, Dendrolimus sibericus, Desmiafuneralis, Diaphania hyalinata, Diaphania nitidalis, Diatraea grandiosella, Diatraea saccharalis, Ennomos subsignaria, Eoreuma loftini, Ephestia elutella, Erannis tiliaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantria cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrsisalis,* Malacosoma sp., *Mamestra brassicae, Mamestra configurata, Manduca quinquemaca, Manduca sexta, Maruca testulalis, Melanchra picta, Operophtera brumata,* Orgyia sp., *Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Playnota flouendana, Platynota sultana, Platyptilia cardutaactyla, Plodia interpunctella, Plutella xylostella, Pontia protodice, Pseudaletia unipuncta, Pseudoplusia includens, Sabulodes aegrotata, Schizura concinna, Sitotroga cerealella, Spilonota ocellana,* Spodoptera sp., *Syngraphafalcifera, Thaurnstopoeapityocampa, Tineola bisselliella, Trichoplusia ni, Udea rubigalis, Xylomyges curialis, Yponomeuta padella;.* The compositions of the invention may also be effective against insect pests of the order Coleoptera, e.g., Leptinotarsa sp., *Acanthoscelides obtectus, Callosobruchus chinensis, Epilachna varivestis, Pyrrhalta luteola, Cylas formicarius elegantulus, Listronotus oregonensis,* Sitophilus sp., *Cyclocephala borealis, Cyclocephala immaculata, Macrodactylus subspinosus, Popillia japonica, Rhizotrogus majalis, Alphitobius diaperinus, Palorus ratzeburgi, Tene-* brio molitor, Tenebrio obscurus, Triboliwn castaneum, Tribolium confum, Triboliiis destructor, Diptera, e.g., Aedes sp., Andes vittatus, Anastrepha ludens, Anastrepha su-spensa, Anopheles barberi, Anopheles quadrimaculatus, Armigeres subalbatus, Calliphora stygian, Calliphora vicina, Ceratitis capitata, Chironomus tentans, Chrysomya rufifacies, Cochiiomyia macellaria, Culex sp., Culiseta inornata, Dacus oleae, Delia antiqua, Delia platura, Delia radicum, Drosophila melanogaster, Eupeodes corollae, Glossina austeni, Glossina brevipalpis, Glossina fuscipes, Glossina morsitans centralis, Glossina mnorsitans morsitans, Glossina morsitans submorsitans, Glossina pallidipes, Glossina palpalis gambiensis, Glossina palpalis palpalis, Glossina tachinoides, Haemagogus equinus, Haematobia irritans, Hypoderma bovis, Hypoderma lineatum, Leucopis ninae, Lucilia cuprina, Lucilia sericata, Lutzomyia longlpaipis, Lutzomyia shannoni, Lycoriella mali, Mayetiola destnictor, Musca autumnalis, Musca domestica, Neobellieria sp., Nephrotoma suturalis, Ophyra aenescens, Phaenicla sericata, Phlebotomus sp., Phormia regina, Sabethes cyaneus, Sarcophaga bullata, Scatophaga stercorarla, Stomaxys calcitrans, Toxorhynchites amboinensis, Tripteroides bambusa; Acari, e.g., Oligonychus pratensis, Panonychus ulmi, Tetranychuis urticae; Hymenoptera, e.g., Iridomyrmex humilis, Solenopsis invicta; Isoptera, e.g., Reticulitermes hesperus, Reticulitermes flavipes, Coptotermes formosanus, Zootermopsis angusticollis, Neotermes connexus, Incisitermes minor, Incisiterines immigrans; Siphonaptera, e.g., Ceratophyllus gallinae, Ceratophyllus niger, Nosopsyllus fasciatus, Leptopsylla segnis, Ctenocephalides canis, Ctenocephalides felis, Echicnophaga gallinacea, Pulex irritans, Xenopsylla cheopis, Xenopsylla vexabilis, Tunga penetrans; and Tylenchida, e.g., Melodidogyne incognita, Pratylenchus penetrans.

The following examples are presented by way of illustration, not by way of limitation.

EXAMPLES

Example 1
Bacterial Strains and Plasmids

Figure 2:
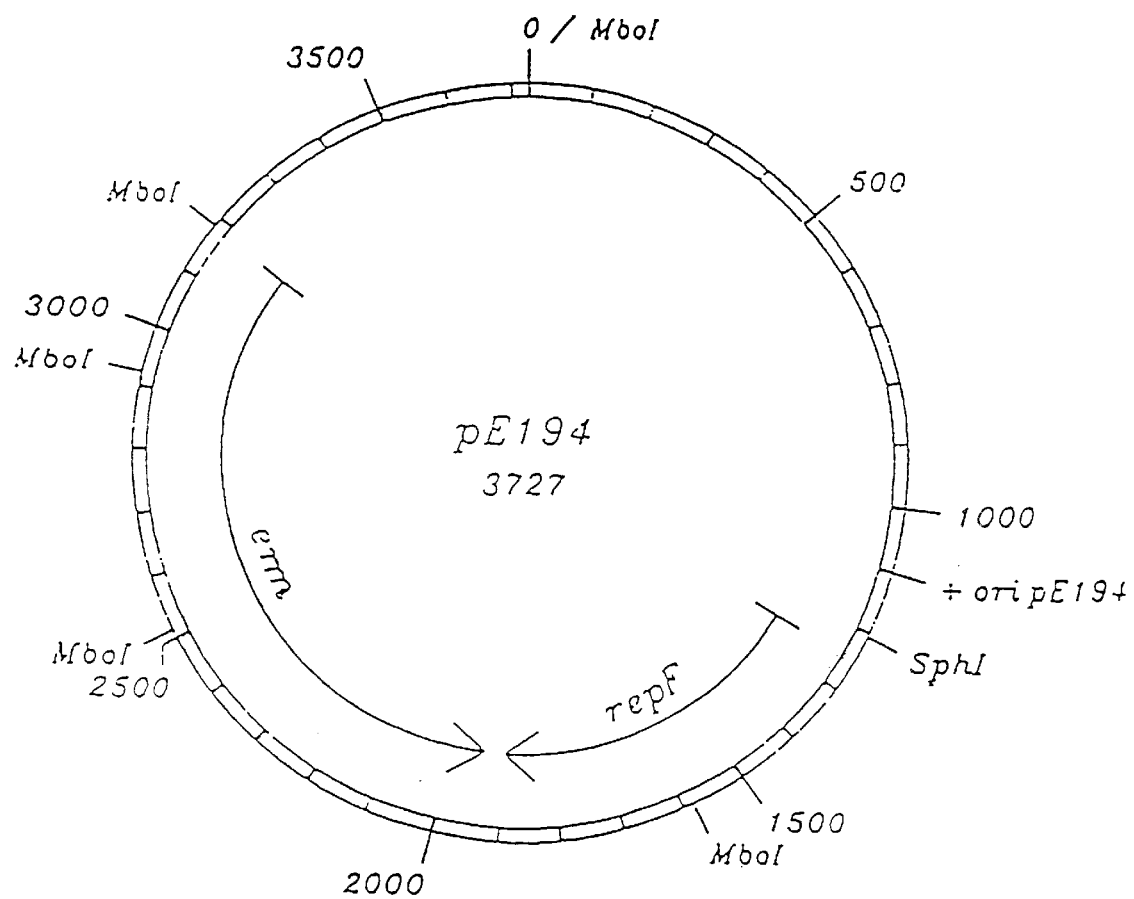
FIG. 2 shows a map of plasmid pE194$^{ts}$.
Figure 5:
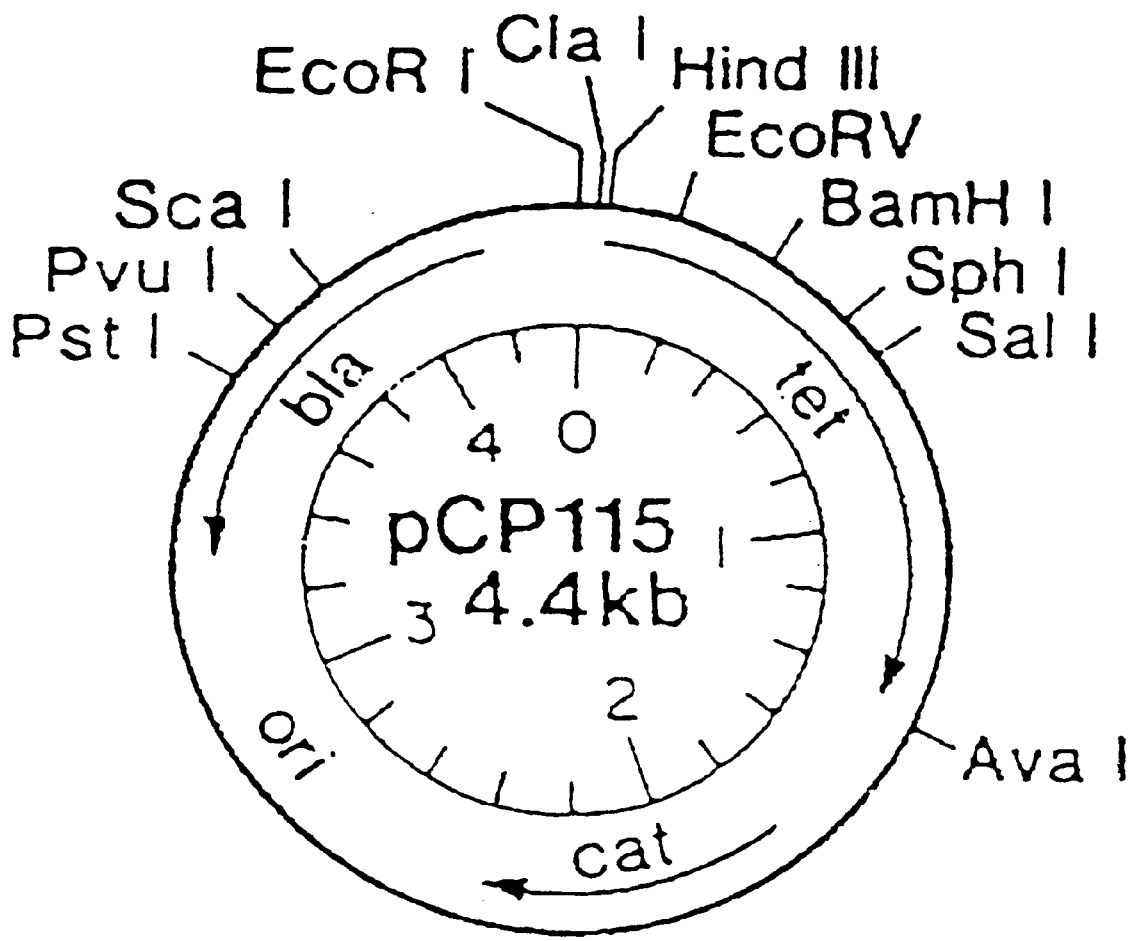
FIG. 5 shows a map of plasmid pCP115.

Bacillus thuringiensis subsp. aizawai EMCC0087 has been deposited with the NRRL and assigned an accession number NRRL B-21147. Bacillus thuringiensis subsp. kurstaki 4D7 and 4D9 (cry- HD-1) are obtained from the Bacillus Genetic Stock Center at Ohio State University. Escherichia coli GM48 dam⁻dcm⁻is disclosed in Yanish-Perron et al., 1985, Gene 33:103–119. E. coli GM272 (Raleigh et al., 1988, Nucl. Acids Res. 16:1563–1575; dam⁻dcm⁻hsd⁻) is obtained from New England Biolabs. Plasmid pBR322 may be obtained through commercial sources. Plasmid pMI1101D is disclosed in Youngman et al., 1984, Plasmid 12:1–9. Plasmid pE194$^{ts}$ is shown in FIG. 2 and is also disclosed in Villafane et al., 1987, J. Bact. 169:4822–4829. Plasmid pCP115 is disclosed in Price and Doi, 1985, Mol. Gen. Genet. 201:88–95 and is shown in FIG. 5.

Figure 3:
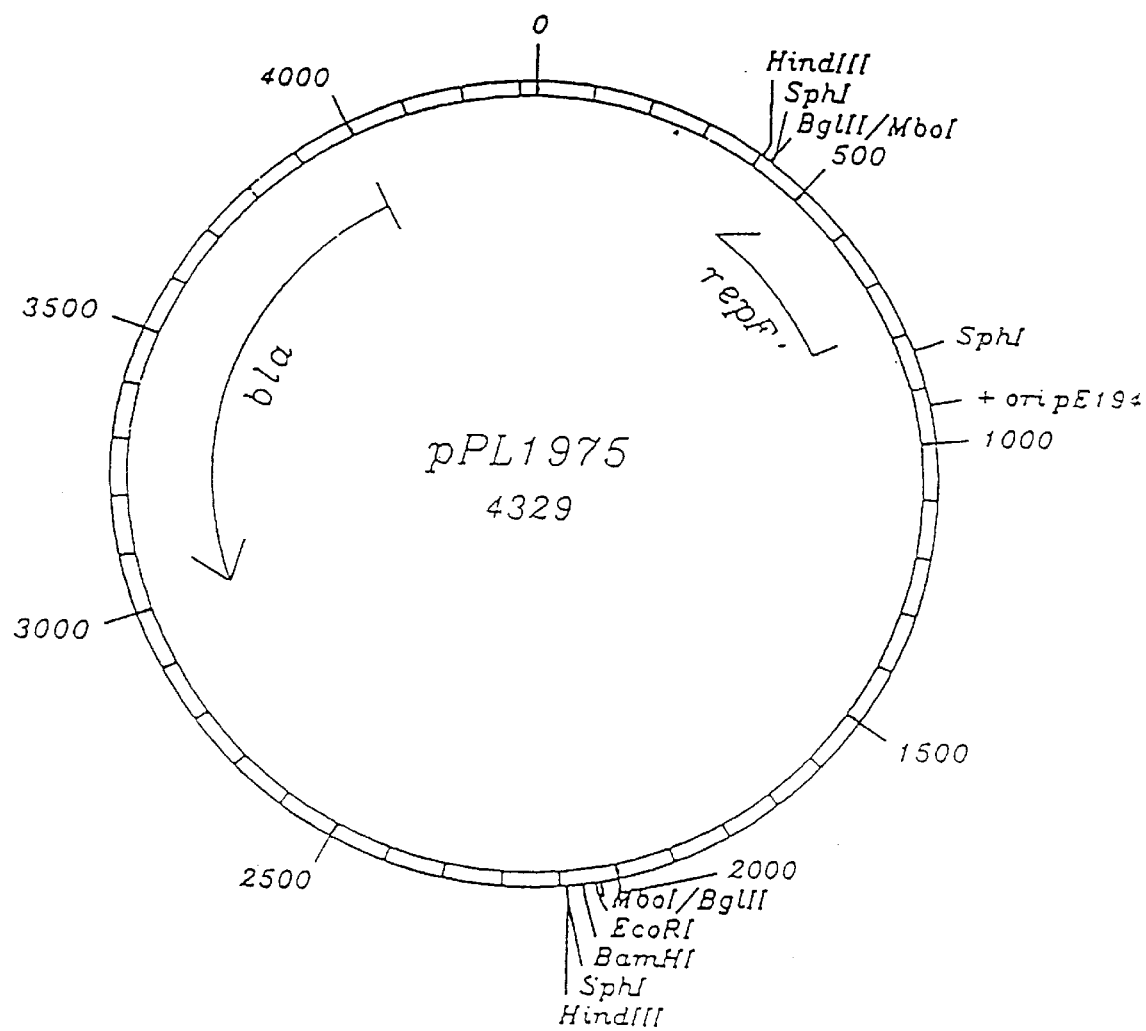
FIG. 3 shows a map of plasmid pPL1975.
Figure 4:
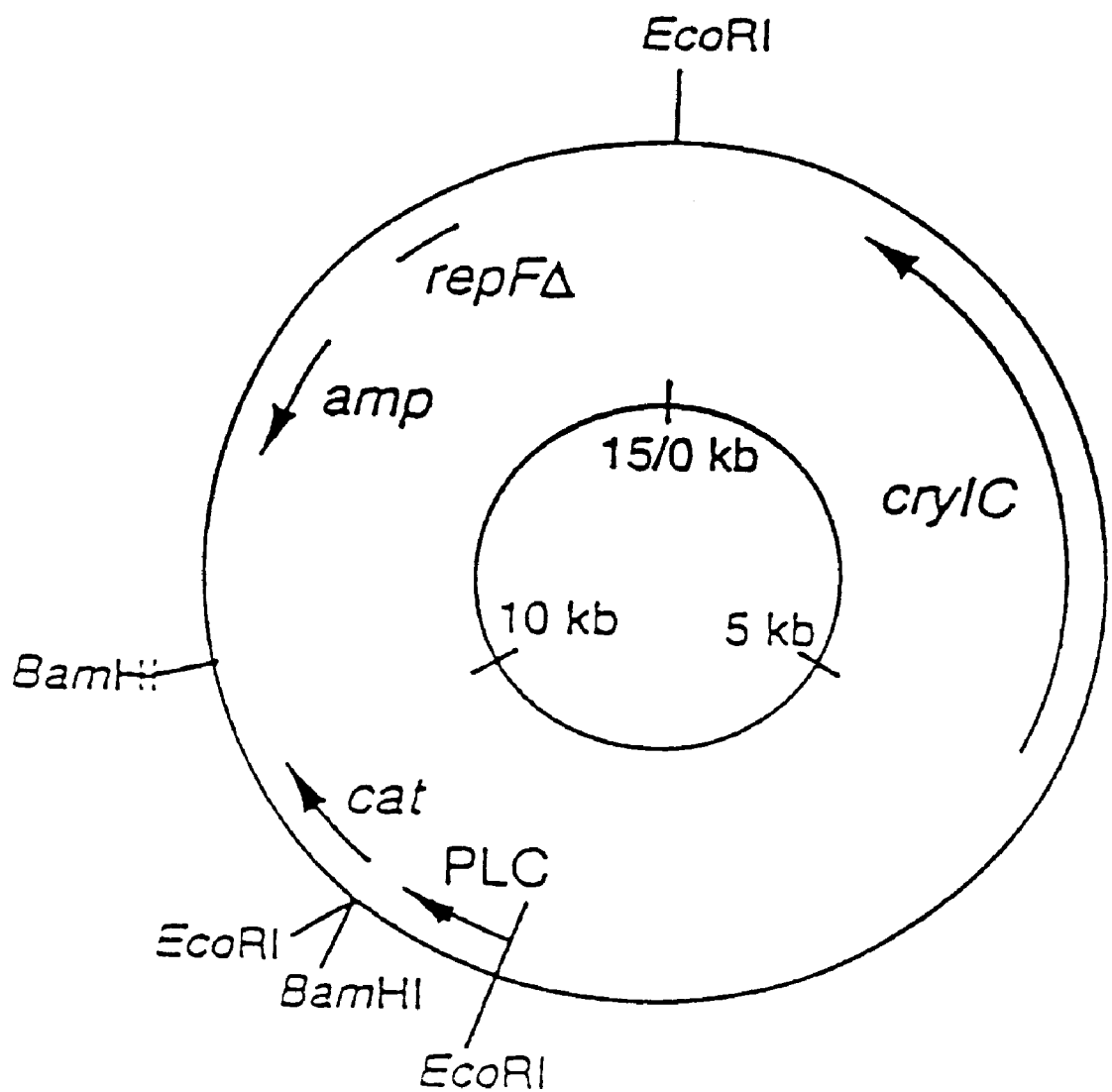
FIG. 4 shows a map of plasmid pET235.

Plasmid pPL1975 is shown in FIG. 3. The following procedure is used to construct pPL1975. Plasmid pDN3000 is constructed by restricting pUC19 (Yanisch-Perron et. al., 1985, Gene 33:103–119) with EcoRI and inserting the following oligonucleotide sequence (prepared by the phosphoamidite method described by Beaucage and Caruthers, 1981, Tetrehedron Let. 22: 1859–1869, on an automatic DNA synthesizer) (SEQ ID NOS:1 and 2)
5'-AATTGATCAAGCTTTAAATGCATGCTAGCAACG CGGCCGCCAACCTCGAGATCTCATG-3'
3'- CTAGTTCGAAATTTACGTACGATCGTTGCGCC GGCGGTTGGAGCTCTAGAGTACTTAA-5'
into the linearized pUC19 followed by ligation. The ligation mixture is then used to transform competent E. coli SJ6 cells and transformants are selected on LB plates containing 100 ug/ml ampicillin. The orientation of the inserted linker in pDN3000 is as indicated by the orientation of the restriction sites in FIG. 1.

Plasmid pPL1975 is constructed by inserting from pE195$^{ts}$ the MboI restriction fragment containing the DNA from position 1 to 1585 into the BglI site of pDN3000. The ligation mixture is then used to transform competent E. coli SJ6 cells and transformants are selected on LB plates containing 100 ug/ml ampicillin. The orientation of these two fragments is as indicated in FIG. 3. pPL1975 thus contains a functional E. coli replication origin and a pE194$^{ts}$ DNA fragment comprising an intact plus origin (+ ori pE194$^{ts}$) and a truncatede repF gene (repF') (Villafane et al., 1987, J. Bact. 169:4822–4829).

Example 2
Preparation of Genomic DNA

Genomic DNA from Bacillus thuringiensis subsp. aizawai EMCC0087 is prepared by inoculating 2 ml LB (Luria-Bertani broth) in a 15×1.5 cm screw-capped test tube with a Bacillus thuringiensis colony. After overnight incubation at 37°0 C. without shaking, the entire tube contents are transferred to a 1 L flask containing 250 ml LB and grown for 6 hours at 37° C. with shaking at 300 rpm. Flask contents are harvested at 8000 rpm in a GSA rotor, and the resulting pellet is resuspended in 20 ml TE buffer (10 mM Tris, pH 7.9, 1 mM EDTA) in a 25 ml Corex centrifuge tube. Approximately 20 mg solid lysozyme is added and the tube contents are mixed by gentle inversion. After a 10 minute incubation at 37°0 C., 1 ml 0.5 M EDTA and 0.5 ml 2 M Tris, pH 7.9 are added. The tube contents are again mixed by gentle inversion and allowed to incubate for an additional 15 minutes. Subsequently, 200 μl RNase A (10 mg/ml) is added, followed by a 15 minute incubation at 37° C. and addition of 2.3 ml of 10% SDS. Proteinase K (2 mg) is added, and the tube contents are incubated for 2 hrs. at 50°0 C., split into two Corex tubes, and extracted at least two times with phenol and two times with phenol/chloroform. Genomic DNA is precipitated with ⅒ volume of sodium acetate and 2.5 volumes of 95% ethanol, and resuspended in approximately 5 ml of TE buffer.

Example 3
Construction of Plasmid pET235

A size-selected library of Bacillus thuringiensis subsp. aizawai EMCC0087 DNA fragments is created by digestion of genomic DNA with EcoRI, gel electrophoresis, excision of fragments 6 kb and larger, and release from the agarose by electroelution. After ligation of the fragments into the EcoRI site of pBR322 and transformation into E. coli strain XL-1 Blue MRF' (Stratagene Cloning Systems; Jerpseth et al., 1992, Strategies 5 [3 ]:81), the 8-kb EcoRI fragment bearing the cryIC gene is cloned by colony blot hybridization as previously described (Sambrook et al., 1989, Molecular Cloning, A Laboratory Manual, Cold Spring Harbor, N.Y.), probing with a DNA fragment corresponding to nucleotides 869 to 1175 of the cryIC gene (Honée et al., 1988, Nucleic Acids Research 16:6240) with the addition of four nucleotides (CGGG) to the 5' end to create a functional BamHI site. This probe is generated by PCR amplification of Bacillus thuringiensis subsp. aizawai EMCCO0087 genomic DNA and is shown below as SEQ ID NO:3.

5'-CGGGATCCACAGTTACAGTCTGTAGCFCAATT
ACCTACTTTTAACGTTA TGGAGAGCAGCCGAATT
AGAAATCCTCACCTTATTTGATATATTGAATAA
TCTTACAATCTTTACGGATTGGTTTAGT-
GTTGGACGCAATTTTTATTGG GGAGGACATC-
GAGTAATATCTAGCCTTATAGGAGGTGG-
TAACATAACA TCTCCTATATATGGAAGAGAGG
CGAACCAGGAGCCTCCAAGATCCTTTA CTTT-
TAATGGACCGGTATTTAGGACTTTATCAAATC
CTACTTTACGATT ATTACAGCAACCTTGGCC-3'

The phospholipase C (plc) gene of *Bacillus thuringiensis* subsp. *kurstaki* 4D7 is PCR amplified using primers containing BamHI sites. The primers are shown below:

5'-TTGGATCCAGGGAAATATTATTTATACGTCTAT
AAATAT-3' (SEQ ID NO:4) 5'-TTGGATCCGA
ATAAAAAATCATGTGGAAACGTCATAG-3' (SEQID
NO:5). The amplified fragment is digested with BamHI and inserted into the BamHI site of pCPl 115. The 850 bp EcoRI-BamHI fragment containing the 3' half of the plc gene is then inserted between the EcoRI and BamHI sites of PL1975. Plasmid pET231 is constructed by insertion of the 8-kb EcoRI fragment bearing the cryIC gene into the EcoRI site of pNNB11. Plasmid pET235 (see FIG. 1) is constructed by insertion of the cat-bearing 1.5-kb BamHI fragment of pMI1101D into the BamHI site of pET231.

Example 4

Integration and Amplification of Plasmid pET235

*E. coli* cells are electroporated with a Bio-Rad Gene Pulser as described by the manufacturer. *Bacillus thuringiensis* subsp. *kurstaki* 4D9 cells are prepared for electroporation by the method of Macaluso and Mettus (1991, *J. Bacteiol.* 173:1353–1356). However, unlike their procedure, no electrical modifications are made to the Gene Pulser, instead, cells are placed in a 0.2 cm cuvette and electroporated at 800 ohms, 25 uF, and 1600 volts (8000 volts per cm). Plasmid DNA for electroporation is prepared in *E. coli* GM272 (dam⁻dcm⁻hsd⁻), which generally yields higher efficiencies for transformation of *Bacillus thuringiensis* than does plasmid DNA prepared from GM48 (dam⁻dcm⁻). *Bacillus thuringiensis* subsp. *kurstaki* 4D9 is transformed with pE194$^{ts}$, and colonies are selected on LB plates containing 5 µg erytiromycin per ml. *Bacillus thuringiensis* subsp. *kurstaki* 4D9 bearing helper plasmid pE194$^{ts}$ is transformed with pET235, and colonies are selected on LB plates containing 10 µg chloramphenicol per ml. Integrants are formed by incubating the transformants at 37° C. to cure them of pE194$^{ts}$. Erythromycin sensitive colonies are subsequently serially plated at 30 and 60 µg choramphenicol per ml. Integrant EMCC0122 is selected based on crystal size as determined by phase-contrast light microscopy as described supra.

Example 5

Determination of Crystal Size of *Bacillus thuringiensis* subsp. *kurstaki* 4D9 cryIC IntegrantEMCC0122

Crystal measurements are made by photographing spore/crystal preparations with a Zeiss Axioscope, and then printing the negatives at a final magmfication of approximately 2000×. Measurements of the crystals in millimeters are made with a ruler, and then normalized to the average length of the spores in each photo to account for any differences in photo enlargement. Assuming that a mature endospore is approximately 1 µm in its longest diameter, then the crystals have the dimensions indicated in Table 1.

The results are shown in Table 1, infra.

TABLE 1

| | Crystal Dimensions of cryIC Integrant EMCC0122 | | | | | |
| --- | --- | --- | --- | --- | --- | --- |
| Sample | Crystal Length (µm) | Range (µm) | Crystal Width (µm) | Range (µm) | Crystal Volume (µm³) | Number Measured |
| EMCC0122 | 1.0 ± 0.17 | 0.74 ± 1.4 | 0.60 ± 0.083 | 0.45–0.76 | 0.12 ± 0.055 | 20 |

Example 6

Cultivation of *Bacillus thuringiensis* subsp. *kurstaki* 4D9 cryIC Integrant EMCC0122

A subculture of *Bacillus thuringiensis* subsp. *kurstaki* 4D9 cryIC integrant EMCC0122, maintained as a 40% glycerol stock stored at −80° C., is used to inoculate 250 ml baffled shake flasks containing 50 ml of P/Y medium, having the following composition.

| | |
| --- | --- |
| Citric acid | 1.0 g/l |
| KH$_2$PO$_4$ | 1.3 g/l |
| CaCl$_2$.H$_2$O | 0.33 g/l |
| MgSO$_4$.7H$_2$O | 0.67 g/l |
| Maltrin-100 | 20 g/l |
| Yeast Extract | 10 g/l |
| Peptone | 15.3 g/l |
| Trace metals | 0.3 ml/l |

The pH of the medium is adjusted to 7.0 using 10 N NaOH.

After inoculation, shake flasks are inoculated at 30° C. on a rotary shaker with 250-rpm shaking for 72 hours. The whole cultures are stabilized by addition of 10 mg potassium sorbate, 3 mg sodium benzoate, and 0.5 mg methyl paraben per ml culture, adjusted to pH 4.5 with 30% H$_3$PO$_4$ and stored at 5° C.

Example 7

Bioassay of Crystal Delta-endotoxins from *Bacillus thuringiensis* subsp. *kurstaki* 4D9 cryIC Integrant EMCC0122 against *Spodobtera exigua*

The potency of the *Bacillus thuringiensis* subsp. *kurstaki* cryIC integrant EMCC0122 is determined by diet incorporation bioassay using third instar *Spodoptera exigua* larvae.

The *Bacillus thuringiensis* subsp. *kurstaki* integrant ECCM0122 whole broth from EXAMPLE 6 is serially diluted to establish the range of potency. A reference standard, *Bacillus thuringiensis* subsp. *aizawai* EMCC0087 cultivated as described in EXAMPLE 6, is also run.

Standard artificial diet composed of water, agar, sugar, casein, wheat germ, methyl paraben, sorbic acid, linseed oil, cellulose, salts, and vitamins are prepared in a 20 liter kettle.

This provides enough diet to test 10 to 12 samples with seven different concentrations of a test substance. The *Bacillus thuringiensis* subsp. *kurstaki* integrant EMCC0122 whole broth preparation is serially diluted to give 16 ml aliquots. Each aliquot is added to 184 g of molten diet The mixture is subsequently homogenized and then poured into a plastic tray bearing 40 individual wells. Three control trays are prepared for each batch of diet Once the diet has cooled and solidified, one third instar *Spodoptera exigua* larva is added to each well, and the trays are covered with a perforated sheet of clear mylar. The trays are placed on racks and incubated for four days at 28° C. and 65% humidity.

After four days, insect mortality is rated. Each tray is given a sharp blow against a table top, and larvae that do not move are counted as dead. Per cent mortality is calculated and the data is analyzed via parallel probit analysis. LC50 values, LC90 values, the slope of the regression lines, coefficient of variation (CV), and potencies in Spodoptera Units (SU) are determnined. Samples are run a minimum of 3 times or until three potencies are within 20% of a calculated mean for each sample.

The results are shown in Table 2, infra. The potency of ECCM0122 is approximately 2 times that of *Bacillus thuringiensis* subsp. *aizawai* EMCC0087.

TABLE 2

Potency of cryIC Integrant EMCC0122 on *Spodoptera exigua*

| Sample | LC50 | LC90 | Slope | CV | SU |
|--------|------|------|-------|------|------|
| EMCC0087 | 3127 | 16922 | 2.1 | 10.2 | 750 |
| EMCC0122 | 2074 | 8021 | 2.2 | 9.7 | 1671 |

DEPOSIT OF MICROORGANISMS

The following strains of *Bacillus thuringiensis* have been deposited in the Agricultural Research Service Patent Culture Collection, Northern Regional Research Laboratory (NRRL), 1815 University Street, Peoria, Ill. 61604, USA.

| Strain | Accession Number | Deposit Date |
|--------|------------------|--------------|
| EMCC0087 | NRRL B-21147 | October 6, 1993 |
| EMCC0122 | NRRL B-21386 | January 19, 1995 |

The strains have been deposited under conditions that assure that access to the culture will be available during the pendency of this patent application to one determined by the Commissioner of Patents and Trademarks to be entitled thereto under 37 C.F.R §1.14 and 35 U.S.C. §122. The deposit represents a substantially pure culture of each deposited strain. The deposit is available as required by foreign patent laws in countries in which counterparts of the subject application, or its progeny are filed. However, it should be understood that the availability of a deposit does not constitute a license to practice the subject invention in derogation of patent rights granted by governmental action.

Further, the subject culture deposit will be stored and made available to the public in accordance with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for obtaining an integrant of *Bacillus thuringienis* comprising:

(a) introducing into a cell of a host *Bacillus thuringiensis* strain (i) a first DNA vector comprising a first origin of replication and at least one function gene encoding at least one temperature sensitive replication protein required for plasmid replication from said first origin of replication, and (ii) a second DNA vector comprising a second origin of replication and a selectable marker but lacking a functional gene or portion thereof encoding a factor required for plasmid replication from the second origin of replication, as well as a heterologous DNA sequence encoding a *Bacillus thuringinesis* delta-endotoxin, and a DNA sequence that is homologous with a region of the genome of said parental strain, wherein said second vector cannot replicate in the absence of said first vector and (b) culturing the cell of step (a) under selective conditions of temperature and antibiotic pressure leading to integration of said second DNA vector into the genome of said parental cell by homologous recombination and loss of the first DNA vector.

2. The method according to claim 1 in which the host *Bacillus thuringiensis* strain is a cry⁻ strain.

3. The method according to claim 1 in which the host *Bacillus thuringiensis* strain is selected from the group consisting of *Bacillus thuringiensis* subsp. *kurstaki*, *Bacillus thuringiensis* subsp. *aizawai*, *Bacillus thuringiensis* subsp. *galleriae*, *Bacillus thuringiensis* subsp. *entomocidus*, *Bacillus thuringiensis* subsp. *tenebrionis*, *Bacillus thuringiensis* subsp. *thuringiensis*, *Bacillus thuringiensis* subsp. *alesti*, *Bacillus thuringiensis* subsp. *canadiensis*, *Bacillus thuringiensis* subsp. *darmstadiensis*, *Bacillus thuringiensis* subsp. *dendrolimus*, *Bacillus thuringiensis* subsp. *finitimus*, *Bacillus thuringiensis* subsp. *kenyae*, *Bacillus thuringiensis* subsp. *morrisoni*, *Bacillus thuringiensis* subsp. *subtoxicus*, *Bacillus thuringiensis* subsp. *toumanoffi*, *Bacillus thuringiensis* subsp. *toumanoffi*, *Bacillus thuringiensis* subsp. *pondicheriensis*, *Bacillus thuringiensis* subsp. *shandogiensis*, *Bacillus thuringiensis* subsp. *sotto*, *Bacillus thuringiensis* subsp. *nigeriae*, *Bacillus thuringiensis* subsp. *yunnanensis*, *Bacillus thuringiensis* subsp. *dakota*, *Bacillus thuringiensis* subsp. *indiana*, *Bacillus thuringiensis* subsp. *tohokuensis*, *Bacillus thuringiensis* subsp. *kumamotoensis*, *Bacillus thuringiensis* subsp. *tochigiensis*, *Bacillus thuringiensis* subsp. *t hompsoni*, *Bacillus thuringiensis* subsp. *wuhanensis*, *Bacillus thuringiensis* subsp. *kyushuensis*, *Bacillus thuringiensis* subsp. *ostriniae*, *Bacillus thuringien-* sis subsp. *tolworthi*, *Bacillus thuringiensis* subsp. *pakistani*, *Bacillus thuringiensis* subsp *japonensis*, *Bacillus thuringiensis* subsp. *colmeri*, *Bacillus thuringiensis* subsp. *pondicheriensis*, *Bacillus thuringiensis* subsp. *shandongiensis*, *Bacillus thuringiensis* subsp. *neoleonensis*, *Bacillus thuringiensis* subsp. *coreanensis*, *Bacillus thuringiensis* subsp. *silo*, *Bacillus thuringiensis* subsp. *mexcanensis*, and *Bacillus thuringiensis* subsp. *israelensis*.

4. The method according to claim 1 in which the host *Bacillus thuringiensis* strain is *Bacillus thuringiensis* subsp. *kurstaki*.

5. The method according to claim 1 in which the DNA sequence encoding a delta-endotoxin is a cryIC gene.

6. The method according to claim 1 in which the DNA sequence encoding the delta-endotoxin is obtained from a *Bacillus thuringiensis* strain selected from the group consisting of *Bacillus thuringiensis* subsp. *kurstaki*, *Bacillus thuringiensis* subsp. *aizawai*, *Bacillus thuringiensis* subsp. *galleriae*, *Bacillus thuringiensis* subsp. *entomocidus*, *Bacillus thuringiensis* subsp. *tenebrionis*, *Bacillus thuringiensis* subsp. *thuringiensis*, *Bacillus thuringiensis* subsp. *alesti*, *Bacillus thuringiensis* subsp. *canadiensis*, *Bacillus thuringiensis* subsp. *darmnstadiensis*, *Bacillus thuringiensis* subsp. *dendrolimus*, *Bacillus thuringiensis* subsp. *finitimus*, *Bacillus thuringiensis* subsp. *kenyae*, *Bacillus thuringiensis* subsp. *morrisoni*, *Bacillus thuringiensis* subsp. *subtoxicus*, *Bacillus thuringiensis* subsp. *toumanoffi*, *Bacillus thuringiensis* subsp. *toumanoffi*, *Bacillus thuringiensis* subsp. *pondicheriensis*, *Bacillus thuringiensis* subsp. *shandogiensis*, *Bacillus thuringiensis* subsp. *sotto*, *Bacillus thuringiensis* subsp. *nigeriae*, *Bacillus thuringiensis* subsp. *yunnanensis*, *Bacillus thuringiensis* subsp. *dakota*, *Bacillus thuringiensis* subsp. *indiana*, *Bacillus thuringiensis* subsp. *tohokuensis*, *Bacillus thuringiensis* subsp. *kumamotoensis*, *Bacillus thuringiensis* subsp. *tochigiensis*, *Bacillus thuringiensis* subsp. *thompsoni*, *Bacillus thuringiensis* subsp. *wuhanensis*, *Bacillus thuringiensis* subsp. *kyushuensis*, *Bacillus thuringiensis* subsp. *ostriniae*, *Bacillus thuringiensis* subsp. *tolworthi*, *Bacillus thuringiensis* subsp. *pakistani*, *Bacillus thuringiensis* subsp. *japonensis*, *Bacillus thuringiensis* subsp. *colmeri*, *Bacillus thuringiensis* subsp. *pondicheriensis*, *Bacillus thuringiensis* subsp. *shandongiensis*, *Bacillus thuringiensis* subsp. *neoleonensis*, *Bacillus thuringiensis* subsp. *coreanensis*, *Bacillus thuringiensis* subsp. *silo*, *Bacillus thuringiensis* subsp. *mexcanensis*, and *Bacillus thuringiensis* subsp. *israelensis*.

7. The method according to claim 1 in which the DNA sequence encoding the delta-endotoxin is obtained from *Bacillus thuringiensis* subsp. *aizawai*.

8. The method according to claim 1 in which the selectable marker from the second DNA vector is a DNA sequence encoding antibiotic resistance.

9. The method according to claim 1 in which the first DNA vector further comprises a selectable marker and in which said selectable marker differs from the selectable marker in the second DNA vector.

10. The method according the claim 1, in which the first DNA vector comprises a first origin of replication from a single-strand DNA plasmid and a functional rep gene, and in which the second DNA vector comprises a second origin of replication from a single-strand DNA plasmid but lacking a functional rep gene, a DNA sequence encoding a *Bacillus thuringiensis* delta-endotoxin, and a DNA sequence that is homologous with a region of the genome of said host strain.

11. The method according to claim 1 in which the cell in step (b) is incubated at about 37° C.

12. The method according to claim 1 in which said method further comprises amplifying the integrated DNA sequence by culturing the integrant of step (b) in the presence of increasing amounts of a selecting-agent.

13. The method according to claim 1 in which the integrant has all of the identifying characteristics of strain EMCC0122, deposited with the NRRL, having an accession number of NRRL B-21386.

* * * * *